(12) United States Patent
Quinn et al.

(10) Patent No.: US 7,207,981 B2
(45) Date of Patent: *Apr. 24, 2007

(54) MULTI-EXCHANGE CATHETER GUIDE MEMBER WITH IMPROVED SEAL

(75) Inventors: David Quinn, Salthill (IE); Kevin Boyle, Renmore (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 10/880,302

(22) Filed: Jun. 28, 2004

(65) Prior Publication Data

US 2005/0288701 A1  Dec. 29, 2005

(51) Int. Cl.
*A61M 25/00* (2006.01)
*A61M 31/00* (2006.01)
*A61M 29/00* (2006.01)

(52) U.S. Cl. .................. 604/528; 604/103.04; 604/523; 606/191; 606/192; 600/585

(58) Field of Classification Search ............ 604/96.01, 604/97.01, 95.05, 95.03, 528, 103.04; 606/191–198; 600/434, 585
See application file for complete search history.

(56) References Cited

U.S. PATENT DOCUMENTS

| | | | |
|---|---|---|---|
| 4,988,353 A | | 1/1991 | Gross ........................ 606/192 |
| 4,988,356 A * | | 1/1991 | Crittenden et al. ......... 606/192 |
| 5,324,269 A * | | 6/1994 | Miraki ....................... 604/160 |
| 5,549,554 A * | | 8/1996 | Miraki ................... 604/101.05 |
| 6,248,092 B1 * | | 6/2001 | Miraki et al. ............ 604/96.01 |
| 6,905,477 B2 * | | 6/2005 | McDonnell et al. ... 604/103.04 |
| 2003/0191491 A1 | | 10/2003 | Duane et al. .............. 606/194 |
| 2004/0059291 A1 | | 3/2004 | McDonnell et al. ... 604/103.04 |
| 2004/0059369 A1 | | 3/2004 | Duffy et al. ................ 606/194 |
| 2004/0122363 A1 | | 6/2004 | Gribbons et al. ...... 604/103.04 |
| 2005/0222603 A1 * | | 10/2005 | Andreas et al. ............. 606/194 |

* cited by examiner

*Primary Examiner*—Nicolas D. Lucchesi
*Assistant Examiner*—Aamer S. Ahmed

(57) ABSTRACT

A catheter and a guidewire exchange system includes a catheter and a guide member. The catheter includes a lumen extending through the shaft and sized to receive the guidewire, and a longitudinal guideway enabling transverse access from the shaft exterior surface to the lumen. The guide member includes a housing, a catheter passageway extending through the housing and adapted to slidably receive the catheter, a guidewire passageway extending from one end of the housing into the catheter passageway and including a tube adapted to merge the guidewire transversely through the guideway and into the first lumen, a rigid nose cone attached to the housing and having an aperture extending therethrough that is continuous with the catheter passageway and adapted to slidably receive the catheter, and a first gasket positioned in line with the catheter passageway and tightenable to impede catheter movement through the catheter passageway.

6 Claims, 4 Drawing Sheets

MULTI-EXCHANGE CATHETER GUIDE MEMBER WITH IMPROVED SEAL

TECHNICAL FIELD

The present invention generally relates to medical catheters and medical apparatuses involving medical catheters. The present invention more particularly relates to multi-exchange catheters with improved guide members.

BACKGROUND

Cardiovascular disease, including atherosclerosis, is a leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA." The objective in angioplasty is to enlarge the lumen of the affected coronary artery by radial hydraulic expansion. The procedure is accomplished by inflating a balloon of a balloon catheter within the narrowed lumen of coronary artery.

In addition to PTCA, catheters are used for delivery of stents or grafts, therapeutic drugs (such as anti-vaso-occlusion agents or tumor treatment drugs) and radiopaque agents for radiographic viewing. Other uses for such catheters are well known in the art.

The anatomy of coronary arteries varies widely from patient to patient. Often a patient's coronary arteries are irregularly shaped, highly tortuous and very narrow. The tortuous configuration of the arteries may present difficulties to the physician in proper placement of a guidewire, and advancement of a catheter to a treatment site. A highly tortuous coronary anatomy typically will present considerable resistance to advancement of the catheter over the guidewire.

Therefore, it is important for a catheter to be highly flexible. However, it is also important for a catheter shaft to be stiff enough to push the catheter into the vessel in a controlled manner from a position far away from the distalmost point of the catheter.

Catheters for PTCA and other procedures may include a proximal shaft, a transition section and a distal shaft having a flexible distal tip. In particular, the catheters have a proximal shaft, which is generally rigid for increased pushability and a more flexible distal shaft with a flexible distal tip for curving around particularly tortuous vessels. The proximal shaft may be made stiff by the insertion of a thin biocompatible tube, such as a stainless steel hypotube, into a lumen formed within the proximal shaft. The transition section is the portion of the catheter between the stiffer proximal shaft and the more flexible distal shaft, which provides a transition in flexibility between the two portions.

With some types of catheter construction, when an increase in resistance occurs during a procedure there is a tendency for portions of the catheter to collapse, buckle axially or kink, particularly in an area where flexibility of the catheter shaft shifts dramatically. Consequently, the transition section is often an area where the flexibility of the catheter gradually transitions between the stiff proximal shaft and the flexible distal shaft. It is known in the art to create a more gradual flexibility transition by spiral cutting a distal end of the hypotubing used to create stiffness in the proximal shaft. Typically, the spiral cut is longitudinally spaced farther apart at the hypotube proximal end creating an area of flexibility, and longitudinally spaced closer together at the hypotube distal end creating an area of even greater flexibility.

In a typical PTCA procedure, it may be necessary to perform multiple dilatations, for example, using various sized balloons. In order to accomplish the multiple dilatations, the original catheter must be removed and a second catheter tracked to the treatment site. When catheter exchange is desired, it is advantageous to leave the guidewire in place while the first catheter is removed to properly track the second catheter.

Two types of catheters commonly used in angioplasty procedures are referred to as over-the-wire (OTW) catheters and rapid exchange (RX) catheters. A third type of catheter with preferred features of both OTW and RX catheters, which is sold under the trademarks MULTI-EXCHANGE, ZIPPER MX, ZIPPER, MX and/or MXII, is discussed below. An OTW catheter's guidewire lumen runs the entire length of the catheter and may be positioned next to, or enveloped within, an inflation shaft. Thus, the entire length of an OTW catheter is tracked over a guidewire during a PTCA procedure. A RX catheter, on the other hand, has a guidewire lumen that extends within only the distalmost portion of the catheter. Thus, during a PTCA procedure only the distalmost portion of a RX catheter is tracked over a guidewire.

If a catheter exchange is required while using a standard OTW catheter, the user must add an extension wire onto the proximal end of the guidewire to maintain control of the guidewire, slide the catheter off of the extended guidewire, slide the new catheter onto the guidewire and track back into position. Multiple operators are required to hold the extended guidewire in place while the original catheter is exchanged in order to maintain its sterility.

A RX catheter avoids the need for multiple operators when exchanging the catheter. With a rapid exchange catheter, the guidewire runs along the exterior of the catheter for all but the distalmost portion of the catheter. As such, the guidewire can be held in place without an extension when the catheter is removed from the body. However, one problem associated with RX catheters is the guidewire, and most of the catheter, must be removed from the body in order to exchange guidewires. Essentially the procedure must then start anew because both the guidewire and the catheter must be retracked to the treatment site. An OTW catheter, with the guidewire lumen extending the entire length of the catheter, allows for simple guidewire exchange.

A balloon catheter capable of both fast and simple guidewire and catheter exchange is particularly advantageous. A catheter designed to address this need is sold by Medtronic Vascular, Inc. of Santa Rosa, Calif. under the trademarks MULTI-EXCHANGE, ZIPPER MX, ZIPPER, MX and/or MXII (hereinafter referred to as the "MX catheter"). An MX catheter is disclosed in U.S. Pat. No. 4,988,356 to Crittenden et al.; co-pending U.S. patent application Ser. No. 10/116,234, filed Apr. 4, 2002; co-pending U.S. patent application Ser. No. 10/251,578, filed Sep. 18, 2002; co-pending U.S. patent application Ser. No. 10/251,477, filed Sep. 20, 2002; co-pending U.S. patent application Ser. No. 10/722,191, filed Nov. 24, 2003; and co-pending U.S. patent application Ser. No. 10/720,535, filed Nov. 24, 2003, all of which are incorporated by reference in their entirety herein.

The MX catheter includes a catheter shaft having a guidewire lumen positioned side-by-side with an inflation lumen. The MX catheter also includes a longitudinal cut that extends along the catheter shaft and that extends radially from the guidewire lumen to an exterior surface of a catheter shaft. A guide member through which the shaft is slidably coupled cooperates with the longitudinal cut such that a guidewire may extend transversely into or out of the guidewire lumen at any location along the longitudinal cut's length. By moving the shaft with respect to the guide member, the effective over-the-wire length of the MX catheter is adjustable.

The guidewire is threaded into a guidewire lumen opening at the distal end of the catheter and out through the guide member. The guidewire lumen envelopes the guidewire as the catheter is advanced into the patient's vasculature while the guide member and guidewire are held stationary. Furthermore, the indwelling catheter may be removed by withdrawing the catheter from the patient while holding the proximal end of the guidewire and the guide member in a fixed position. When the catheter has been withdrawn to the point where the distal end of the cut has reached the guide member, the distal portion of the catheter over the guidewire is of a sufficiently short length that the catheter may be drawn over the proximal end of the guidewire without releasing control of the guidewire or disturbing its position within the patient.

While the MX Catheter provides many advantages over RX and OTW catheters, the oval shaft may not be the most secure in the hemostatic valve. Furthermore, there remains the possibility that air may enter the patient through the hemostatic valve if it is not sealed sufficiently. For example, an exemplary known dye injection procedure includes tracking the catheter over the guidewire until the tip of the catheter is positioned at the distal tip of the guide catheter. During this stage of the procedure the manifold between the dye source and the guide catheter is closed. Next, the Y-adaptor, or hemostasis valve, is placed onto the proximal catheter shaft. The manifold is then opened to allow dye or other contrast media into a syringe. The manifold is again closed, and the syringe is opened. However, prior to injecting the dye, blood must be drawn into the syringe from the guide catheter in order to remove any air bubbles that may have been introduced during the guidewire insertion or catheter insertion. However, when blood is drawn into the syringe a vacuum is created in the proximally disposed guide member, thereby creating an opportunity for unwanted air aspiration into the guidewire lumen if a very heavy vacuum is drawn. Additionally, if an RX catheter is used with a passive/active gasket in a hemostasis valve, air aspiration may occur if the gasket is not properly closed onto the catheter shaft and a heavy vacuum is drawn.

Accordingly, it is desirable to provide an apparatus or system that improves shaft stability within the hemostasis valve and prevents gas aspiration. It is also desirable to provide such an apparatus or system that can be implemented with a currently used catheter guide tool. In addition, it is desirable to provide such an apparatus that does not slow down guidewire insertion, contrast media injection, or other medical processes involving the catheter. Furthermore, other desirable features and characteristics of the present invention will become apparent from the subsequent detailed description and the appended claims, taken in conjunction with the accompanying drawings and the foregoing technical field and background.

BRIEF SUMMARY

A system is provided for exchanging a catheter and guidewire in a patient. The system comprises a catheter and a guide member. The catheter comprises an elongate shaft having an exterior surface, a proximal end, and a distal end; a first lumen extending through the shaft from the shaft proximal end to the shaft distal end, and sized to receive a guidewire; and a longitudinal guideway extending distally from the shaft proximal end, and enabling transverse access from the shaft exterior surface to the first lumen. The guide member comprises a housing having a proximal end and a distal end; a catheter passageway extending through the housing from the proximal end to the distal end and adapted to slidably receive the catheter; a guidewire passageway extending from the housing proximal end into the catheter passageway, and comprising a tube adapted to merge the guidewire transversely through the guideway and into the first lumen; a rigid nose cone attached to the housing and having an aperture extending therethrough that is continuous with the catheter passageway and adapted to slidably receive the catheter; and a first gasket positioned in line with the catheter passageway, and tightenable to impede catheter movement through the catheter passageway.

An apparatus is also provided for advancing and retracting a guidewire and a catheter having a lumen, an exterior surface, and a longitudinal guideway that enables transverse access from the catheter exterior surface to the lumen. The apparatus comprises a housing having a proximal end and a distal end; a catheter passageway extending through the housing from the proximal end to the distal end and adapted to slidably receive the catheter; a guidewire passageway extending from the housing proximal end into the catheter passageway, and comprising a tube adapted to merge the guidewire transversely through the guideway and into the first lumen; a rigid nose cone attached to the housing and having an aperture extending therethrough that is continuous with the catheter passageway and adapted to slidably receive the catheter; and a first gasket positioned in line with the catheter passageway, and tightenable to impede catheter movement through the catheter passageway.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
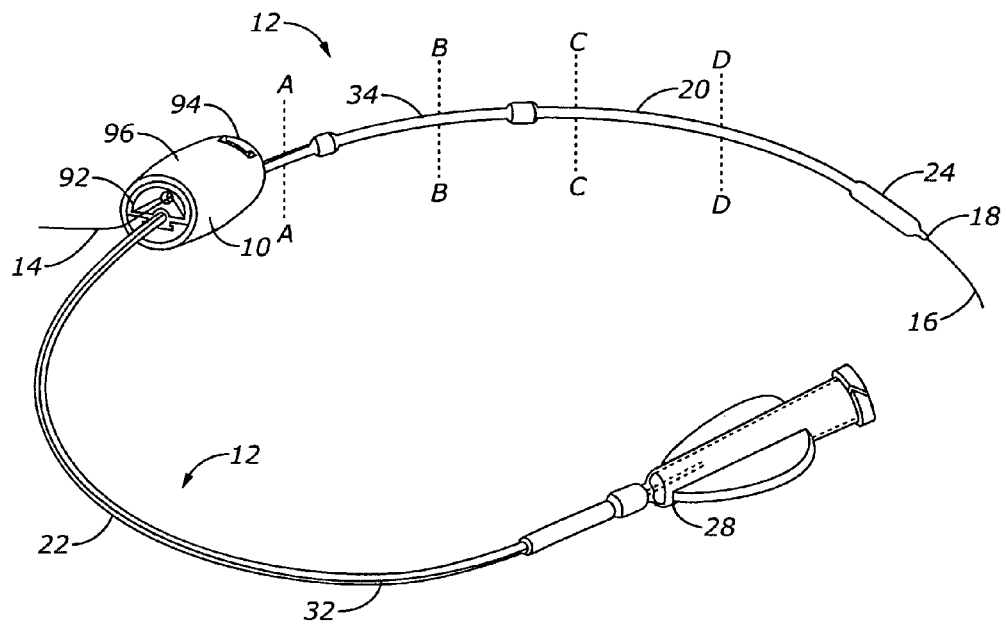
FIG. 1 is a perspective view of a guide member with a guide wire extending through a guide member and into a catheter according to the present invention.

The present invention is used with an MX catheter, an exemplary embodiment of which is illustrated in FIG. 1. The catheter 12 includes an elongate, flexible, cylindrical main body having a distal shaft 20 and a proximal shaft 22. According to the present embodiment, the catheter 12 is a delivery catheter for such procedures as PTCA or stent delivery and has a balloon 24 mounted around the catheter body near the catheter distal end 18. The balloon 24 may be inflated and deflated through the catheter inflation lumen 26. The inflation lumen 26 communicates with a fitting 28 at the catheter proximal end, and extends the catheter length to terminate in communication with the balloon interior at the catheter distal end 18. The catheter 12 also includes a guidewire lumen 30 that receives the guidewire 14 and extends the entire catheter length. A longitudinal cut extends into the guidewire lumen 30 along the length of most of the proximal shaft 22 to form a guideway 32. The proximal shaft distal section 34 does not include the guideway 32. The guidewire lumen 30 and the inflation lumen 26 are coaxially arranged in the distal shaft 20 according to the present embodiment.

The present invention includes a guide member for the MX catheter 12. FIG. 1 depicts a guide member 10 according to an embodiment of the invention, with a guide wire 14 extending through the guide member 10 and into the MX catheter 12. FIGS. 2A to 2D are cross sections of the catheter 12 at points A—A, B—B, C—C, and D—D along the catheter length. The guide member 10 serves as a juncture in which the catheter 12 and guidewire 14 may be merged or separated so that the guidewire portion that extends proximal to the guide member 10 is separated from the catheter 12, and the guidewire portion that is located distal to the guide member 10 is contained and housed within the catheter, although the guidewire distal end 16 may protrude out of the catheter distal end 18.

Figure 2A:
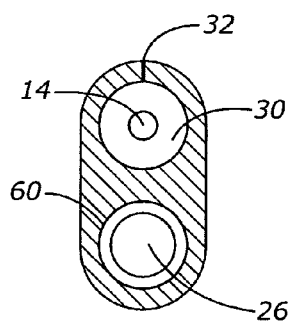
FIGS. 2A–D are cross sectional views of a catheter at points A—A, B—B, C—C, and D—D illustrated in FIG. 1.
Figure 2B:
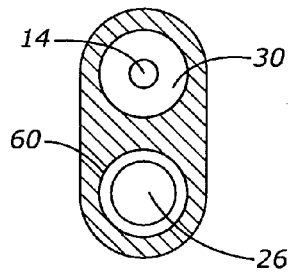
Figure 2C:
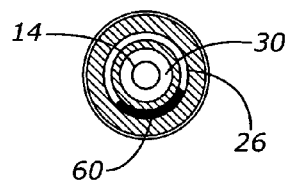
Figure 2D:
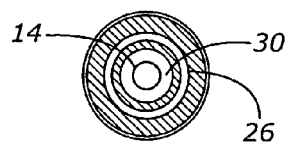
Figure 3:
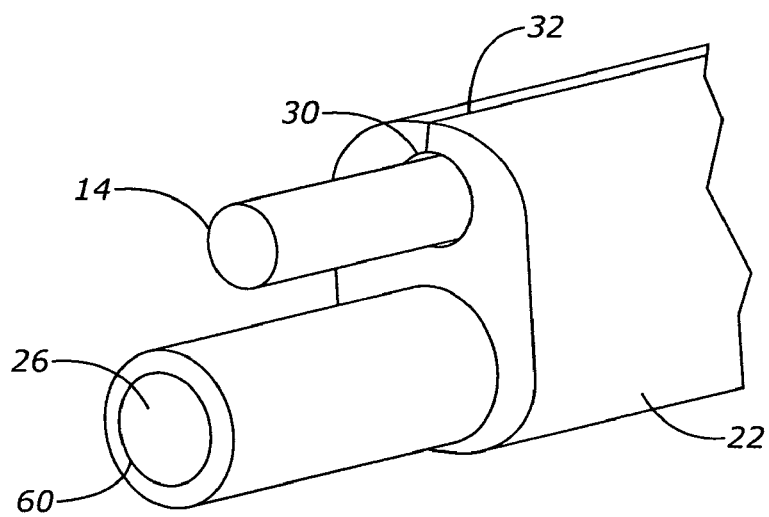
FIG. 3 is a perspective cross sectional view of an oval proximal shaft.
Figure 4:
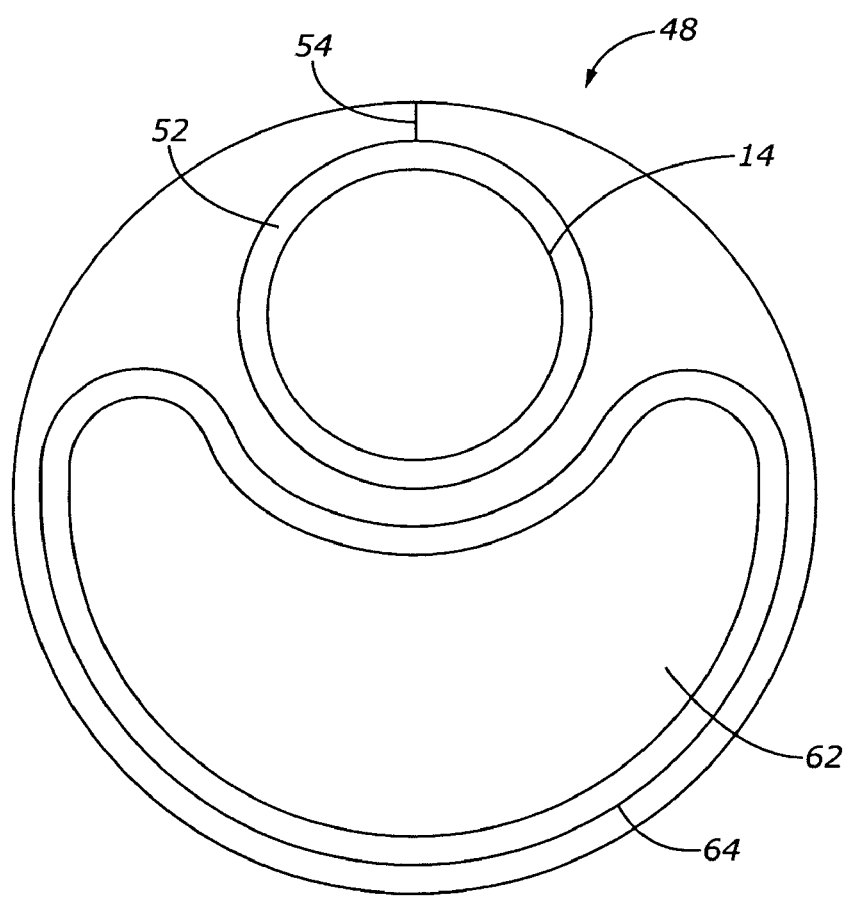
FIG. 4 is a cross sectional view of a circular proximal shaft.

The catheter proximal shaft 22 described above can be modified to suit various needs. For example, the proximal shaft can be a tri-lumen shaft to provide passage for various drugs, fluids, wires, or other necessary compositions or equipment. Further, the proximal shaft may be oval, circular, or other suitable shape. FIG. 3 is a perspective cross sectional view of an oval proximal shaft 22 according to one embodiment of the invention, and FIG. 4 is a cross sectional view of a circular proximal shaft 48 according to another embodiment of the invention. Each of the proximal shafts 22, 48 has a respective guidewire lumen 30, 52 that is accessible through a guideway 32, 54 located along the proximal shaft length. Each of the proximal shafts 22, 48 also includes an inflation lumen 26, 62 that extends side by side with the guidewire lumen 30, 52 along the proximal shaft length. The inflation lumens 26, 62 are preferably supported by a stiffening member 60, 64 such as a hypotube. The inflation lumen 62 in the embodiment depicted in FIG. 4 is crescent shaped and the hypotube stiffening member 64 also is formed in the same shape to withstand force transmission along the catheter length. The stiffening members may further include a transition section at their respective distal sections in conjunction with a transition between the relatively stiff proximal shaft to the relatively flexible distal shaft and avoid shaft kinking at the junction therebetween. For example, the hypotube 60 may be skived at its distal end, with the skived portion extending into the distal section as depicted in FIG. 2C.

Returning to FIG. 1, the proximal shaft 22 can be formed from suitable biomedical grade materials such as polyethylene, cross-linked polyethylene, polyolefins, polyamides, blends of polyamides and polyolefins, fluoropolymers, polyesters, polyketones, polyimides, polysulphones, polyoxymethylenes, and compatibilizers based on polyolefins, including grafted polyolefins, and other comparable materials. A lubrication additive may also be used with any polymer and may include polyethylene micro-powders, fluoropolymers, silicone based oils, fluoro-ether oils, molybdenum disulphide and polyethylene oxide. Additionally, a reinforcing additive may be used such as nano-clays, graphite, carbon fibers, glass fibers, and polymeric fibers. The distal shaft 20 can be made of a suitable polyethylene or polyolefin that readily bonds to the proximal shaft 22.

Figure 5:
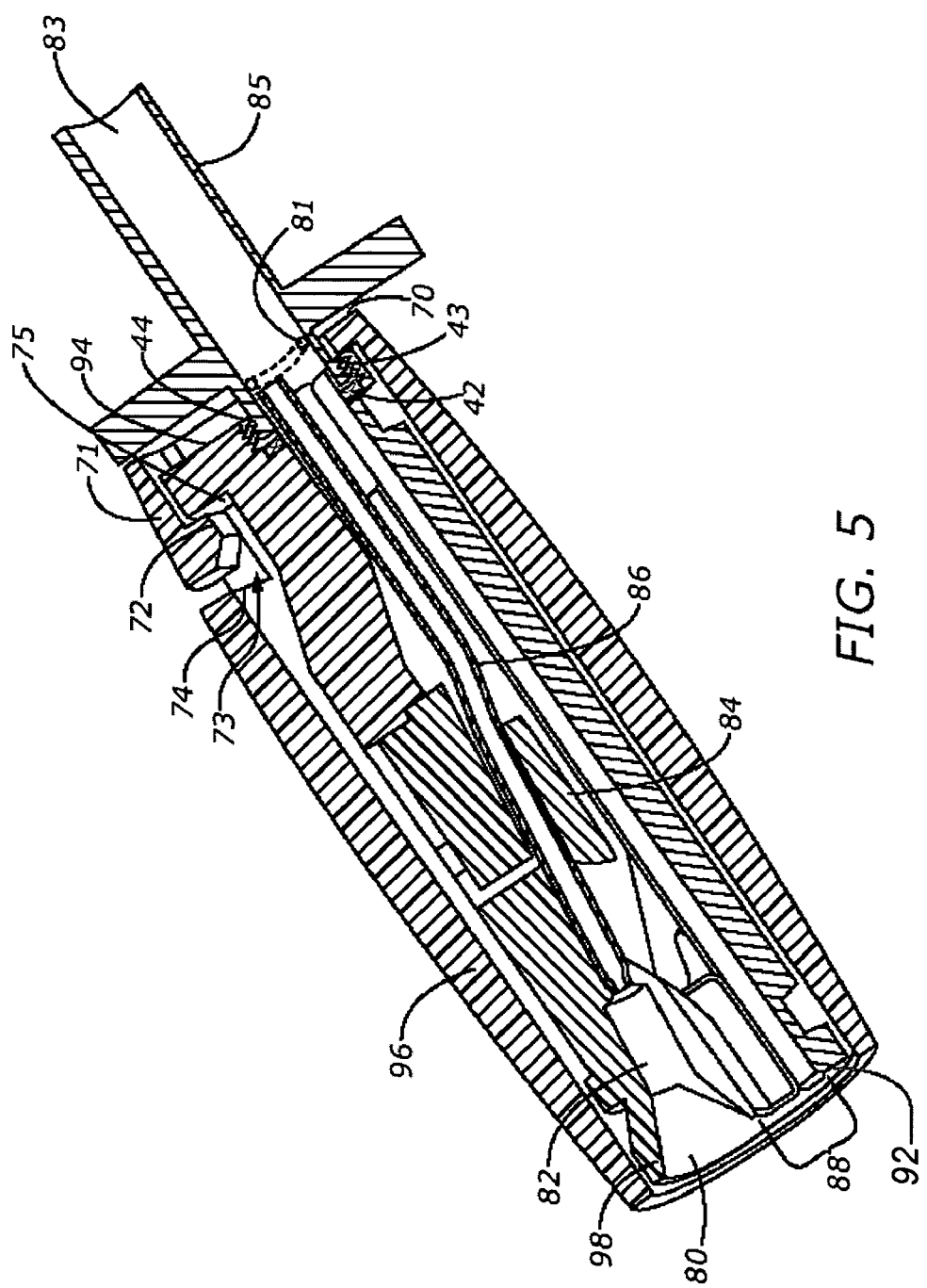
FIG. 5 is a sectional view of a guide member and its components according to an embodiment of the present invention.

Turning now to FIG. 5, the guide member 10 and its components will be discussed according to one embodiment of the invention. The guide member 10 surrounds the proximal shaft 22 and includes proximal and distal ends 92, 94. An outer tubular member 96 freely rotates around an inner main body 98 and hence is decoupled from the inner main body 98. An inwardly extending distal annular wall 70 prevents the main body 98 from slipping out of the outer member 96. A retaining clip 71 includes a tab 72 that extends into a space 73 formed by two main body walls 74, 75. Additional tabs may be used as necessary to retain the inner main body 98 within the tubular member 96.

The guide member main body 98 includes a catheter passageway 88 extending longitudinally in a generally straight line from the guide member proximal end 92 to the guide member distal end 94. A guidewire passageway 80 extends distally from the guide member proximal end 92 through an entrance port 82 into a tube 86 and then into the catheter guidewire lumen 30, although the catheter is not depicted in FIG. 5. The catheter passageway 88 is configured to slidingly receive the proximal shaft 22, and has a cross sectional shape that approximates the proximal shaft exterior shape, whether the proximal shaft is circular, oval, triangular, shamrock shaped, or otherwise shaped. The catheter passageway 88 enlarges in a central area to provide space for a keel 84 that is aligned with the passageway 80 and positioned to spread the catheter guideway 32 and extend into the catheter guidewire lumen 30 to enable guidewire insertion during use.

A rigid nose cone 85 is attached to the guide member distal end 94. The nose cone 85 includes an elongate aperture 83 extending through the nose cone 85 in line with the catheter passageway 88. The aperture 83 is configured to slidingly receive the proximal shaft 22, and can have a cross sectional shape that approximates the proximal shaft exterior shape, although the cross sectional shape may be any shape that size that allows the proximal shaft 22 to advance and retract therethrough in a substantially frictionless manner. The nose cone outer surface has a circular cross sectional shape in an exemplary embodiment of the invention in order to provide a substantially air tight seal with a hemostatis valve clamp as described in detail below. The nose cone 85 may attach to the guide member distal end 94 using any known attachment device, although the components are attached using threaded regions 43, 44 in the embodiment depicted in FIG. 5. In one exemplary embodiment employing the threaded regions 43, 44 an elastic clamping gasket 42 is disposed between the nose cone 85 and the guide member distal end 94, and by rotating the nose cone 85 in a tightening direction the clamping gasket 42 is longitudinally compressed. In another embodiment of the invention, the clamping gasket 42 is compressed using a mechanism that locks the nose cone into a compressing position when the nose cone is pressed toward the guide member distal end 94. When the clamping gasket 42 is compressed in a longitudinal direction, the gasket inner diameter is constricted around the proximal shaft 22 to secure the catheter 21 in a stationary position. The clamping gasket can have an inner diameter or other inner cross sectional shape that approximates the proximal shaft outer surface.

At the guide member proximal end 92, the entrance port 82 is configured to mate with a conventional wire introducer tool and is tapered to aid in loading such a tool. The tube 86 may vary in its length, although in an exemplary embodiment of the invention the tube 86 extends through the catheter guidewire lumen 30 approximately thirty-five millimeters past the guide member distal end 94. The tube 86 may be formed from a flexible material such as a polyimide, and particularly the tube region that extends through the catheter guidewire lumen 30. In one embodiment of the invention the tube region that introduces the guidewire 14 into the guidewire lumen 30 may be substantially rigid to provide the necessary support for the guidewire 14.

The guide member 10 is made of blends of polyamides and polyolefins in an exemplary embodiment of the invention. Other exemplary materials include ceramics, metals such as stainless steel, and other polymers such as polyamides and liquid crystal polymers. Lubrication additives such as polyethylene micro-powders, fluoropolymers, silicone-based oils, fluoro-ether oils, molybdenum disulphide, and polyethylene oxide may be included. Reinforcing additives such as nano-clays, graphite, carbon fibers, glass fibers, polyesters, polyketones, polyimides, polysulphones, polyoxymethylenes, polyolefins, cross-linked polyolefins may also be included, along with compatibilizers based on polyolefins, such as grafted polyolefins, ceramics, and metals.

Figure 6:
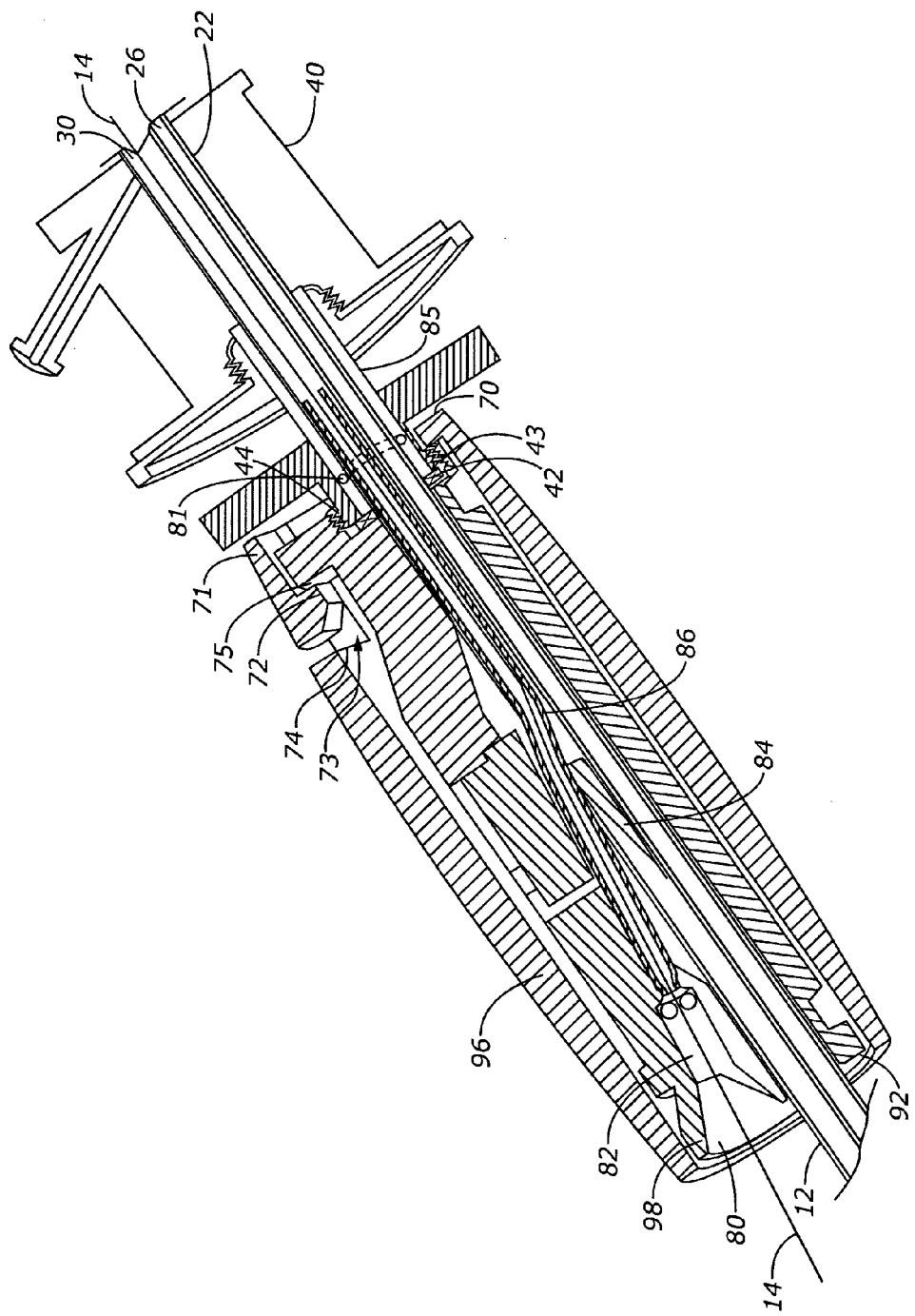
FIG. 6 is a sectional view of the catheter and the guide member equipped with a nose cone and various gaskets according to an embodiment of the present invention.

An exemplary guide member operation will now be described, although the procedures in the following description clearly set forth only one of many operations enabled by the guide member 10. The exemplary guide member operation is discussed with reference to FIG. 6, which is a sectional view of the guide member 10, a Touhy adaptor or hemostasis valve 40, and a catheter 12 extending through the catheter passageway and the hemostasis valve 40 with a guidewire 14 being directed into the guidewire lumen 30. After the guidewire 14 and a guide catheter (not shown) are inserted into a patient, the catheter 12 is inserted with a backloading operation. The guidewire 14 is inserted into the catheter distal end 18 and threaded proximally through the guidewire lumen 30 until the guidewire tube 86 captures the guidewire proximal end and directs it into the passageway 80 and then out of the guide member proximal end 92. This procedure can be accomplished with the guide member 10 adjacent the catheter guideway distal end.

As the distal shaft 20 enters the patient, the guide member 10 can be brought near the hemostasis valve 40. The guide member 10 is seated adjacent to the hemostasis valve 40 and is equipped with a rigid nose cone 85 that surrounds the distal shaft and is inserted into the hemostasis valve 40. The proximal shaft 22 is then advanced through the guide member, and the keel 84 engages the catheter guideway 32. After the catheter 12 is inserted, the hemostasis valve 40 is tightened to create a substantially air tight seal with the nose cone 85. If a wire change is required, one simply withdraws the guidewire 14 from the guide member 10 as the guide member 10 is seated against the valve and as the proximal shaft 22 remains in the patient. A new guidewire is then inserted into the catheter through the passageway 80. If a catheter exchange is required, one simply holds the guidewire 14 in place and begins moving the proximal shaft 22 proximally through the guide member. The catheter can then be removed, and another catheter may then be backloaded onto the guidewire 14 and introduced into the patient as described above.

Without the rigid nose cone 85 surrounding the proximal shaft 22, the hemostasis valve 40 would typically clamp directly onto the proximal shaft 22, and the tube 86 extending into the proximal shaft 22 would also be subjected to the clamping force. However, the rigid nose cone 85 prevents any clamping force from being exerted on the proximal shaft 22 and allows the catheter 12 to be advanced and retracted as necessary without any frictional resistance from the hemostasis valve 40.

During a dye or other contrast media injection, an air tight seal is required around the proximal shaft 22. Since the nose cone 85 is rigidly disposed around the proximal shaft 22 and prevents the hemostasis valve 40 from forming such a seal, the nose cone 85 can be rotated in a tightening direction and thereby cause the clamping gasket 42 to constrict around the proximal shaft 22 and create a substantially air tight seal with the shaft exterior. Further, tightening the clamping gasket 42 causes the guidewire lumen 30 to constrict around the tube 86. With the gasket 42 in a tightened state, an air tight seal is formed between the shaft exterior and the clamping gasket 42, between the tube 86 and the guidewire lumen 30, and between the nose cone 85 and the hemostasis valve 40. After dye or other contrast media is injected, the clamping gasket 42 can be loosened to allow the catheter 12 to again be freely advanced and retracted.

As mentioned above, a significant advantage provided by the gasket 42 is the ability to tighten or loosen the hemostasis valve 40 without affecting the ability for the catheter 12 to advance or retract. Rather, the clamping gasket 42 regulates the amount of friction force applied to the catheter 12 when the nose cone 85 is tightened or loosened, and consequently regulates the ability for the catheter 12 to advance or retract. Using conventional assemblies having a hemostasis valve 40 that directly clamps the catheter 12, a physician or other user must continually adjust the hemostasis valve 40 in order to achieve satisfactory shaft movement ability and backbleed prior to injecting dye or other contrast media. Further, using such contemporary assemblies, the physician or other user must again adjust the hemostasis valve 40 after the dye is injected to balance dye flow and backbleed. Using the assembly of the present invention, backbleed can be passively regulated by simply forming the nose cone aperture 83 cross sectional shape to approximate the proximal shaft exterior surface cross sectional shape. For example, a portion of the nose cone aperture 83 may have a cross sectional shape that is slightly smaller than the proximal shaft exterior surface cross sectional shape in order to compress the proximal shaft 22 and consequently passively regulate backbleed. However, if a slightly tighter fit around the proximal shaft 22 is necessary, a gasket 81 may be disposed inside the nose cone 85 as another passive seal. The gasket 81 can be an annular body, but should have an aperture that has a cross sectional shape that approximates, and is preferably slightly more constricted than, the cross sectional shape of the proximal shaft exterior surface in order to minimally affect shaft movement.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A catheter and guidewire exchange system, comprising:
   a catheter, comprising:
   an elongate shaft having an exterior surface, a proximal end, and a distal end,
   a first lumen extending through the shaft from the shaft proximal end to the shaft distal end, and sized to receive a guidewire, and
   a longitudinal guideway extending distally from the shaft proximal end, and enabling transverse access from the shaft exterior surface to the first lumen; and
   a guide member, comprising:
   a housing having a proximal end and a distal end,
   a catheter passageway extending through the housing from the proximal end to the distal end and adapted to slidably receive the catheter,
   a guidewire passageway extending from the housing proximal end into the catheter passageway, and comprising a tube adapted to merge the guidewire transversely through the guideway and into the first lumen,
   a rigid nose cone attached to the housing and having an aperture extending therethrough that is continuous with the catheter passageway and adapted to slidably receive the catheter, and
   a first gasket positioned in line with the catheter passageway, and tightenable to impede catheter movement through the catheter passageway and further comprising a second gasket positioned inside the nose cone aperture and having an aperture extending through that is adapted to slidingly receive the catheter.

2. The system according to claim 1, wherein the second gasket aperture has a cross sectional shape that approximates a shaft exterior surface cross sectional shape.

3. The system according to claim 2, wherein the second gasket aperture has a smaller cross sectional shape than the shaft exterior surface cross sectional shape.

4. An apparatus for advancing and retracting a guidewire and a catheter having a lumen, an exterior surface, and a longitudinal guideway that enables transverse access from the catheter exterior surface to the lumen, the apparatus comprising:
   a housing having a proximal end and a distal end,
   a catheter passageway extending through the housing from the proximal end to the distal end and adapted to slidably receive the catheter,
   a guidewire passageway extending from the housing proximal end into the catheter passageway, and comprising a tube adapted to merge the guidewire transversely through the guideway and into the first lumen, and
   a rigid nose cone attached to the housing and having an aperture extending therethrough that is continuous with the catheter passageway and adapted to slidably receive the catheter, and
   a first gasket positioned in line with the catheter passageway, and tightenable to impede catheter movement through the catheter passageway and further comprising a second gasket positioned inside the nose cone aperture and having an aperture extending through that is adapted to slidingly receive the catheter.

5. The apparatus according to claim 4, wherein the second gasket aperture has a cross sectional shape that approximates a shaft exterior surface cross sectional shape.

6. The apparatus according to claim 5, wherein the second gasket aperture has a smaller cross sectional shape than the shaft exterior surface cross sectional shape.

* * * * *